(12) United States Patent
Schlebusch et al.

(10) Patent No.: US 12,311,160 B2
(45) Date of Patent: May 27, 2025

(54) METHOD AND SYSTEM FOR DETERMINING THE SPEED OF SOUND IN A FLUID IN THE REGION OF A CARDIAC SUPPORT SYSTEM

(71) Applicant: KARDION GMBH, Stuttgart (DE)

(72) Inventors: Thomas Alexander Schlebusch, Renningen (DE); Tobias Schmid, Stuttgart (DE)

(73) Assignee: Kardion GmbH, Stuttgart (DE)

( * ) Notice: Subject to any disclaimer, the term of this patent is extended or adjusted under 35 U.S.C. 154(b) by 951 days.

(21) Appl. No.: 15/734,322

(22) PCT Filed: Jun. 6, 2019

(86) PCT No.: PCT/EP2019/064803
§ 371 (c)(1),
(2) Date: Jun. 14, 2021

(87) PCT Pub. No.: WO2019/234163
PCT Pub. Date: Dec. 12, 2019

(65) Prior Publication Data
US 2021/0339002 A1    Nov. 4, 2021

(30) Foreign Application Priority Data
Jun. 6, 2018 (DE) .......................... 102018208899.3

(51) Int. Cl.
*A61B 8/08* (2006.01)
*A61B 8/00* (2006.01)
(Continued)

(52) U.S. Cl.
CPC ......... *A61M 60/546* (2021.01); *A61B 8/0883* (2013.01); *A61B 8/12* (2013.01);
(Continued)

(58) Field of Classification Search
None
See application file for complete search history.

(56) References Cited

U.S. PATENT DOCUMENTS

| 3,088,323 | A | 5/1963 | Welkowitz et al. |
| 4,023,562 | A | 5/1977 | Hynecek et al. |

(Continued)

FOREIGN PATENT DOCUMENTS

| CA | 3 122 415 | 7/2020 |
| CN | 1192351 A | 9/1998 |

(Continued)

OTHER PUBLICATIONS

Atkinson et al., "Pulse-Doppler Ultrasound and Its Clinical Application", The Yale Journal of Biology and Medicine, 1977, vol. 50, pp. 367-373.

(Continued)

*Primary Examiner* — Jonathan Cwern
(74) *Attorney, Agent, or Firm* — Knobbe, Martens, Olson & Bear, LLP (57) ABSTRACT

A method for determining the speed of sound in a fluid in the region of an implanted, vascular support system includes sending an ultrasonic signal using an ultrasonic sensor, reflecting the ultrasonic signal on at least one sound reflector, receiving the reflected ultrasonic signal, and determining the speed of sound in the fluid using the ultrasonic signal. The at least one sound reflector may be visible in the field of vision of the ultrasonic sensor and arranged at a defined distance at least to the ultrasonic sensor or to a further sound reflector.

18 Claims, 5 Drawing Sheets

(51) Int. Cl.
  *A61B 8/12*       (2006.01)
  *A61M 60/546*     (2021.01)
(52) U.S. Cl.
  CPC ............ *A61B 8/488* (2013.01); *A61B 8/5223* (2013.01); *A61M 2205/3375* (2013.01); *A61M 2205/702* (2013.01)

(56) References Cited

U.S. PATENT DOCUMENTS

| | | | |
|---|---|---|---|
| 4,103,679 A * | 8/1978 | Aronson | G01S 15/582 |
| | | | 600/456 |
| 4,559,952 A | 12/1985 | Angelsen et al. | |
| 4,680,730 A | 7/1987 | Omoda | |
| 4,781,525 A | 11/1988 | Hubbard et al. | |
| 4,888,011 A | 12/1989 | Kung et al. | |
| 4,889,131 A | 12/1989 | Salem et al. | |
| 4,902,272 A | 2/1990 | Milder et al. | |
| 5,045,051 A | 9/1991 | Milder et al. | |
| 5,269,811 A | 12/1993 | Hayes | |
| 5,289,821 A | 3/1994 | Swartz | |
| 5,456,715 A | 10/1995 | Liotta | |
| 5,527,159 A | 6/1996 | Bozeman, Jr. et al. | |
| 5,581,038 A | 12/1996 | Lampropoulos | |
| 5,613,935 A | 3/1997 | Jarvik | |
| 5,662,115 A | 9/1997 | Torp | |
| 5,676,651 A | 10/1997 | Larson, Jr. et al. | |
| 5,720,771 A | 2/1998 | Snell | |
| 5,752,976 A | 5/1998 | Duffin et al. | |
| 5,766,207 A | 6/1998 | Potter et al. | |
| 5,827,203 A | 10/1998 | Nita | |
| 5,865,759 A | 2/1999 | Koblanski | |
| 5,888,242 A | 3/1999 | Antaki et al. | |
| 5,904,708 A | 5/1999 | Goedeke | |
| 5,911,685 A | 6/1999 | Siess et al. | |
| 5,964,694 A | 10/1999 | Siess et al. | |
| 5,980,465 A | 11/1999 | Elgas | |
| 6,007,478 A | 12/1999 | Siess et al. | |
| 6,024,704 A | 2/2000 | Meador et al. | |
| 6,053,873 A | 4/2000 | Govari et al. | |
| 6,167,765 B1 | 1/2001 | Weitzel | |
| 6,176,822 B1 | 1/2001 | Nix et al. | |
| 6,183,412 B1 | 2/2001 | Benkowski et al. | |
| 6,185,460 B1 | 2/2001 | Thompson | |
| 6,190,324 B1 | 2/2001 | Kieval et al. | |
| 6,210,318 B1 | 4/2001 | Lederman | |
| 6,231,498 B1 | 5/2001 | Pfeiffer et al. | |
| 6,245,007 B1 | 6/2001 | Bedingham et al. | |
| 6,314,322 B1 | 11/2001 | Rosenberg | |
| 6,351,048 B1 | 2/2002 | Schob et al. | |
| 6,398,734 B1 | 6/2002 | Cimochowski et al. | |
| 6,432,136 B1 | 8/2002 | Weiss et al. | |
| 6,438,409 B1 | 8/2002 | Malik et al. | |
| 6,512,949 B1 | 1/2003 | Combs et al. | |
| 6,530,876 B1 | 3/2003 | Spence | |
| 6,540,658 B1 | 4/2003 | Fasciano et al. | |
| 6,540,659 B1 | 4/2003 | Milbocker | |
| 6,561,975 B1 | 5/2003 | Pool et al. | |
| 6,579,257 B1 | 6/2003 | Elgas et al. | |
| 6,602,182 B1 | 8/2003 | Milbocker | |
| 6,605,032 B2 | 8/2003 | Benkowski et al. | |
| 6,652,447 B2 | 11/2003 | Benkowski et al. | |
| 6,731,976 B2 | 5/2004 | Penn et al. | |
| 6,879,126 B2 | 4/2005 | Paden et al. | |
| 6,912,423 B2 | 6/2005 | Ley et al. | |
| 6,949,066 B2 | 9/2005 | Bearnson et al. | |
| 6,984,201 B2 | 1/2006 | Khaghani et al. | |
| 7,010,954 B2 | 3/2006 | Siess | |
| 7,022,100 B1 | 4/2006 | Aboul-Hosn et al. | |
| 7,024,244 B2 | 4/2006 | Muhlenberg et al. | |
| 7,070,555 B2 | 7/2006 | Siess | |
| 7,083,588 B1 | 8/2006 | Shmulewitz et al. | |
| 7,138,776 B1 | 11/2006 | Gauthier et al. | |
| 7,160,243 B2 | 1/2007 | Medvedev | |
| 7,175,588 B2 | 2/2007 | Morello | |
| 7,177,681 B2 | 2/2007 | Xhu | |
| 7,238,151 B2 | 7/2007 | Frazier | |
| 7,396,327 B2 | 7/2008 | Morello | |
| 7,513,864 B2 | 4/2009 | Kantrowitz et al. | |
| 7,520,850 B2 | 4/2009 | Brockway | |
| 7,527,599 B2 | 5/2009 | Hickey | |
| 7,591,777 B2 | 9/2009 | LaRose | |
| 7,744,560 B2 | 6/2010 | Struble | |
| 7,794,384 B2 | 9/2010 | Sugiura et al. | |
| 7,819,916 B2 | 10/2010 | Yaegashi | |
| 7,850,593 B2 | 12/2010 | Vincent et al. | |
| 7,850,594 B2 | 12/2010 | Sutton et al. | |
| 7,856,335 B2 | 12/2010 | Morello et al. | |
| 7,862,501 B2 | 1/2011 | Woodward et al. | |
| 7,951,062 B2 | 5/2011 | Morello | |
| 7,951,129 B2 | 5/2011 | Chinchoy | |
| 7,963,905 B2 | 6/2011 | Salmonsen et al. | |
| 7,988,728 B2 | 8/2011 | Ayre | |
| 8,075,472 B2 | 12/2011 | Zilbershlag et al. | |
| 8,190,390 B2 | 5/2012 | Morello et al. | |
| 8,211,028 B2 | 7/2012 | Karamanoglu et al. | |
| 8,303,482 B2 | 11/2012 | Schima et al. | |
| 8,323,173 B2 | 12/2012 | Benkowsi et al. | |
| 8,435,182 B1 | 5/2013 | Tamura | |
| 8,449,444 B2 | 5/2013 | Poirier | |
| 8,545,380 B2 | 10/2013 | Farnan et al. | |
| 8,585,572 B2 | 11/2013 | Mehmanesh | |
| 8,591,393 B2 | 11/2013 | Walters et al. | |
| 8,594,790 B2 | 11/2013 | Kjellstrom et al. | |
| 8,622,949 B2 | 1/2014 | Zafirelis et al. | |
| 8,657,733 B2 | 2/2014 | Ayre et al. | |
| 8,657,875 B2 | 2/2014 | Kung et al. | |
| 8,715,151 B2 | 5/2014 | Poirier | |
| 8,747,293 B2 | 6/2014 | Arndt et al. | |
| 8,849,398 B2 | 9/2014 | Evans | |
| 8,864,643 B2 | 10/2014 | Reichenbach et al. | |
| 8,864,644 B2 | 10/2014 | Yomtov | |
| 8,876,685 B2 * | 11/2014 | Crosby | A61M 60/816 |
| | | | 600/16 |
| 8,882,477 B2 | 11/2014 | Fritz, IV et al. | |
| 8,888,728 B2 | 11/2014 | Aboul-Hosn et al. | |
| 8,897,873 B2 | 11/2014 | Schima et al. | |
| 8,903,492 B2 | 12/2014 | Soykan et al. | |
| 9,091,271 B2 | 7/2015 | Bourque | |
| 9,297,735 B2 | 3/2016 | Graichen et al. | |
| 9,308,305 B2 | 4/2016 | Chen et al. | |
| 9,345,824 B2 | 5/2016 | Mohl et al. | |
| 9,371,826 B2 | 6/2016 | Yanai et al. | |
| 9,427,508 B2 | 8/2016 | Reyes et al. | |
| 9,474,840 B2 | 10/2016 | Siess | |
| 9,492,601 B2 | 11/2016 | Casas et al. | |
| 9,511,179 B2 | 12/2016 | Casas et al. | |
| 9,555,173 B2 | 1/2017 | Spanier | |
| 9,555,175 B2 | 1/2017 | Bulent et al. | |
| 9,556,873 B2 | 1/2017 | Yanai et al. | |
| 9,566,374 B2 | 2/2017 | Spence et al. | |
| 9,636,442 B2 | 5/2017 | Karmon et al. | |
| 9,656,010 B2 | 5/2017 | Burke | |
| 9,669,142 B2 | 6/2017 | Spanier et al. | |
| 9,669,144 B2 | 6/2017 | Spanier et al. | |
| 9,694,123 B2 | 7/2017 | Bourque et al. | |
| 9,713,701 B2 | 7/2017 | Sarkar et al. | |
| 9,744,282 B2 | 8/2017 | Rosenberg et al. | |
| 9,789,236 B2 | 10/2017 | Bonde | |
| 9,833,550 B2 | 12/2017 | Siess | |
| 9,848,899 B2 | 12/2017 | Sliwa et al. | |
| 9,849,224 B2 | 12/2017 | Angwin et al. | |
| 9,878,087 B2 | 1/2018 | Richardson et al. | |
| 9,943,236 B2 | 4/2018 | Bennett et al. | |
| 9,950,102 B2 | 4/2018 | Spence et al. | |
| 9,974,894 B2 | 5/2018 | Morello | |
| 9,999,714 B2 | 6/2018 | Spanier et al. | |
| 10,010,662 B2 | 7/2018 | Wiesener et al. | |
| 10,022,480 B2 | 7/2018 | Greatrex et al. | |
| 10,029,037 B2 | 7/2018 | Muller et al. | |
| 10,052,420 B2 | 8/2018 | Medvedev et al. | |
| 10,279,093 B2 | 5/2019 | Reichenbach et al. | |
| 10,322,217 B2 | 6/2019 | Spence | |
| 10,342,906 B2 | 7/2019 | D'Ambrosio et al. | |
| 10,350,342 B2 | 7/2019 | Thomas et al. | |

(56) References Cited

U.S. PATENT DOCUMENTS

| | | |
|---|---|---|
| 10,357,598 B2 | 7/2019 | Aboul-Hosn et al. |
| 10,376,162 B2 | 8/2019 | Edelman et al. |
| 10,413,651 B2 | 9/2019 | Yomtov et al. |
| 10,426,879 B2 | 10/2019 | Farnan |
| 10,449,275 B2 | 10/2019 | Corbett |
| 10,500,322 B2 | 12/2019 | Karch |
| 10,525,178 B2 | 1/2020 | Zeng |
| 10,549,020 B2 | 2/2020 | Spence et al. |
| 10,561,771 B2 | 2/2020 | Heilman et al. |
| 10,561,772 B2 | 2/2020 | Schumacher |
| 10,561,773 B2 | 2/2020 | Ferrari et al. |
| 10,632,241 B2 | 4/2020 | Schenck et al. |
| 10,660,998 B2 | 5/2020 | Hodges |
| 10,668,195 B2 | 6/2020 | Flores |
| 10,732,583 B2 | 8/2020 | Rudser |
| 10,857,275 B2 | 12/2020 | Granegger |
| 10,864,308 B2 | 12/2020 | Muller et al. |
| 11,027,114 B2 | 6/2021 | D'Ambrosio et al. |
| 11,067,085 B2 | 7/2021 | Granegger et al. |
| 11,120,908 B2 | 9/2021 | Agnello et al. |
| 11,131,968 B2 | 9/2021 | Rudser |
| 11,147,960 B2 | 10/2021 | Spanier et al. |
| 11,154,701 B2 | 10/2021 | Reyes et al. |
| 11,154,702 B2 | 10/2021 | Kadrolkar et al. |
| 11,185,682 B2 | 11/2021 | Farnan |
| 11,191,945 B2 | 12/2021 | Siess et al. |
| 11,197,618 B2 | 12/2021 | Edelman et al. |
| 11,217,344 B2 | 1/2022 | Agnello |
| 11,235,139 B2 | 2/2022 | Kudlik |
| 11,241,572 B2 | 2/2022 | Dague et al. |
| 11,273,299 B2 | 3/2022 | Wolman et al. |
| 11,285,310 B2 | 3/2022 | Curran et al. |
| 11,285,311 B2 | 3/2022 | Siess et al. |
| 11,298,524 B2 | 4/2022 | El Katerji et al. |
| 11,311,711 B2 | 4/2022 | Casas et al. |
| 11,316,679 B2 | 4/2022 | Agnello |
| 11,320,382 B2 | 5/2022 | Aikawa |
| 11,324,395 B2 | 5/2022 | Banik et al. |
| 11,331,082 B2 | 5/2022 | Itoh et al. |
| 11,337,724 B2 | 5/2022 | Masubuchi et al. |
| 11,338,125 B2 | 5/2022 | Liu et al. |
| 11,351,356 B2 | 6/2022 | Mohl |
| 11,351,357 B2 | 6/2022 | Mohl |
| 11,351,358 B2 | 6/2022 | Nix et al. |
| 11,357,438 B2 | 6/2022 | Stewart et al. |
| 11,357,968 B2 | 6/2022 | El Katerji et al. |
| 11,376,415 B2 | 7/2022 | Mohl |
| 11,376,419 B2 | 7/2022 | Reyes et al. |
| 11,389,639 B2 | 7/2022 | Casas |
| 11,389,641 B2 | 7/2022 | Nguyen et al. |
| 11,413,444 B2 | 8/2022 | Nix et al. |
| 11,413,445 B2 | 8/2022 | Brown et al. |
| 11,420,041 B2 | 8/2022 | Karch |
| 11,439,806 B2 | 9/2022 | Kimball et al. |
| 11,446,481 B2 | 9/2022 | Wolman et al. |
| 11,478,629 B2 | 10/2022 | Harjes et al. |
| 11,517,740 B2 | 12/2022 | Agarwa et al. |
| 11,521,723 B2 | 12/2022 | Liu et al. |
| 11,524,165 B2 | 12/2022 | Tan et al. |
| 11,527,322 B2 | 12/2022 | Agnello et al. |
| 11,529,062 B2 | 12/2022 | Moyer et al. |
| 11,554,260 B2 | 1/2023 | Reyes et al. |
| 11,572,879 B2 | 2/2023 | Mohl |
| 11,574,741 B2 | 2/2023 | Tan et al. |
| 11,577,068 B2 | 2/2023 | Spence et al. |
| 11,581,083 B2 | 2/2023 | El Katerji et al. |
| 11,583,659 B2 | 2/2023 | Pfeffer et al. |
| 11,587,337 B2 | 2/2023 | Lemay et al. |
| 11,590,337 B2 | 2/2023 | Granegger et al. |
| 11,622,695 B1 | 4/2023 | Adriola et al. |
| 11,628,293 B2 | 4/2023 | Gandhi et al. |
| 11,639,722 B2 | 5/2023 | Medvedev et al. |
| 11,648,386 B2 | 5/2023 | Poirer |
| 11,653,841 B2 | 5/2023 | Reyes et al. |
| 11,666,746 B2 | 6/2023 | Ferrari et al. |
| 11,668,321 B2 | 6/2023 | Richert et al. |
| 11,674,517 B2 | 6/2023 | Mohl |
| 11,676,718 B2 | 6/2023 | Agnello et al. |
| 11,684,276 B2 | 6/2023 | Cros et al. |
| 11,684,769 B2 | 6/2023 | Harjes et al. |
| 11,694,539 B2 | 7/2023 | Kudlik et al. |
| 11,694,813 B2 | 7/2023 | El Katerji et al. |
| 11,696,782 B2 | 7/2023 | Carlson et al. |
| 11,707,617 B2 | 7/2023 | Reyes et al. |
| 11,712,167 B2 | 8/2023 | Medvedev et al. |
| 11,754,077 B1 | 9/2023 | Mohl |
| D1,001,145 S | 10/2023 | Lussier et al. |
| D1,001,146 S | 10/2023 | Lussier et al. |
| 11,771,885 B2 | 10/2023 | Liu et al. |
| 11,779,234 B2 | 10/2023 | Harjes et al. |
| 11,781,551 B2 | 10/2023 | Yanai et al. |
| 11,790,487 B2 | 10/2023 | Barbato et al. |
| 11,793,994 B2 | 10/2023 | Josephy et al. |
| 11,806,116 B2 | 11/2023 | Tuval et al. |
| 11,806,517 B2 | 11/2023 | Petersen |
| 11,806,518 B2 | 11/2023 | Michelena et al. |
| 11,813,079 B2 | 11/2023 | Lau et al. |
| 11,818,782 B2 | 11/2023 | Doudian et al. |
| 11,824,381 B2 | 11/2023 | Conyers et al. |
| 11,826,127 B2 | 11/2023 | Casas |
| 11,832,793 B2 | 12/2023 | McWeeney et al. |
| 11,832,868 B2 | 12/2023 | Smail et al. |
| 11,837,364 B2 | 12/2023 | Lee et al. |
| 11,844,592 B2 | 12/2023 | Tuval et al. |
| 11,844,940 B2 | 12/2023 | D'Ambrosio et al. |
| 11,850,073 B2 | 12/2023 | Wright et al. |
| 11,850,414 B2 | 12/2023 | Schenck et al. |
| 11,850,415 B2 | 12/2023 | Schwammenthal et al. |
| D1,012,284 S | 1/2024 | Glaser et al. |
| 11,857,345 B2 | 1/2024 | Hanson et al. |
| 11,864,878 B2 | 1/2024 | Duval et al. |
| 11,872,384 B2 | 1/2024 | Cotter |
| 11,883,207 B2 | 1/2024 | El Katerji et al. |
| D1,014,552 S | 2/2024 | Lussier et al. |
| 11,890,082 B2 | 2/2024 | Cros et al. |
| 11,896,199 B2 | 2/2024 | Lent et al. |
| 11,900,660 B2 | 2/2024 | Saito et al. |
| 11,903,657 B2 | 2/2024 | Geric et al. |
| 11,906,411 B2 | 2/2024 | Graichen et al. |
| 11,911,550 B2 | 2/2024 | Itamochi et al. |
| D1,017,634 S | 3/2024 | Lussier et al. |
| D1,017,699 S | 3/2024 | Moore et al. |
| 11,923,078 B2 | 3/2024 | Fallen et al. |
| 11,923,093 B2 | 3/2024 | Moffitt et al. |
| 11,925,794 B2 | 3/2024 | Malkin et al. |
| 11,931,073 B2 | 3/2024 | Walsh et al. |
| 11,931,528 B2 | 3/2024 | Rohl et al. |
| 11,931,588 B2 | 3/2024 | Aghassian |
| 11,986,274 B2 | 5/2024 | Edelman |
| 12,017,076 B2 | 6/2024 | Tan et al. |
| 12,023,476 B2 | 7/2024 | Tuval et al. |
| 12,029,891 B2 | 7/2024 | Siess et al. |
| 12,059,559 B2 | 8/2024 | Muller et al. |
| D1,043,730 S | 9/2024 | Lussier et al. |
| D1,043,731 S | 9/2024 | Lussier et al. |
| 12,076,544 B2 | 9/2024 | Siess et al. |
| 12,097,016 B2 | 9/2024 | Goldvasser |
| 12,102,815 B2 | 10/2024 | Dhaliwal et al. |
| 12,144,650 B2 | 11/2024 | Spanier et al. |
| 12,144,976 B2 | 11/2024 | Baumbach et al. |
| 12,178,554 B2 | 12/2024 | Stotz et al. |
| 12,179,009 B2 | 12/2024 | El Katerji et al. |
| 12,183,459 B2 | 12/2024 | Agnello et al. |
| 2001/0016686 A1 | 8/2001 | Okada et al. |
| 2001/0037093 A1 | 11/2001 | Benkowski et al. |
| 2001/0039828 A1 | 11/2001 | Shin et al. |
| 2002/0022785 A1 | 2/2002 | Romano |
| 2002/0082585 A1 | 6/2002 | Carroll et al. |
| 2002/0147495 A1 | 10/2002 | Petroff |
| 2002/0151761 A1 | 10/2002 | Viole et al. |
| 2003/0069465 A1 | 4/2003 | Benkowski et al. |
| 2003/0130581 A1 | 7/2003 | Salo et al. |
| 2003/0139643 A1 | 7/2003 | Smith et al. |
| 2003/0167002 A1 | 9/2003 | Nagar et al. |

(56) References Cited

U.S. PATENT DOCUMENTS

| | | |
|---|---|---|
| 2003/0191357 A1 | 10/2003 | Frazier |
| 2003/0199727 A1 | 10/2003 | Burke |
| 2004/0022640 A1 | 2/2004 | Siess et al. |
| 2004/0044266 A1 | 3/2004 | Siess et al. |
| 2004/0065143 A1 | 4/2004 | Husher |
| 2004/0130009 A1 | 7/2004 | Tangpuz |
| 2004/0167376 A1 | 8/2004 | Peters et al. |
| 2004/0167410 A1 | 8/2004 | Hettrick |
| 2004/0225177 A1 | 11/2004 | Coleman et al. |
| 2004/0241019 A1 | 12/2004 | Goldowsky |
| 2004/0260346 A1 | 12/2004 | Overall et al. |
| 2005/0001324 A1 | 1/2005 | Dunn |
| 2005/0019167 A1 | 1/2005 | Nusser et al. |
| 2005/0107658 A1 | 5/2005 | Brockway |
| 2005/0126268 A1 | 6/2005 | Ouriev et al. |
| 2005/0267322 A1 | 12/2005 | LaRose |
| 2006/0030809 A1 | 2/2006 | Barzilay et al. |
| 2006/0108697 A1 | 5/2006 | Wang |
| 2006/0122583 A1 | 6/2006 | Pesach et al. |
| 2006/0196277 A1 | 9/2006 | Allen et al. |
| 2006/0229488 A1 | 10/2006 | Ayre et al. |
| 2006/0287600 A1* | 12/2006 | McEowen .......... A61B 5/14535 600/481 |
| 2006/0287604 A1 | 12/2006 | Hickey |
| 2007/0060787 A1 | 3/2007 | Peters et al. |
| 2007/0069354 A1 | 3/2007 | Dangelmaier |
| 2007/0073352 A1 | 3/2007 | Euler et al. |
| 2007/0088214 A1 | 4/2007 | Shuros et al. |
| 2007/0156006 A1 | 7/2007 | Smith et al. |
| 2007/0255352 A1 | 11/2007 | Roline et al. |
| 2007/0266778 A1 | 11/2007 | Corey et al. |
| 2007/0282209 A1 | 12/2007 | Lui et al. |
| 2007/0299325 A1 | 12/2007 | Farrell et al. |
| 2008/0015517 A1 | 1/2008 | Geistert et al. |
| 2008/0082005 A1 | 4/2008 | Stern et al. |
| 2008/0091239 A1 | 4/2008 | Johansson et al. |
| 2008/0097595 A1 | 4/2008 | Gabbay |
| 2008/0102096 A1 | 5/2008 | Molin et al. |
| 2008/0108901 A1* | 5/2008 | Baba .................. A61B 8/483 600/459 |
| 2008/0108930 A1 | 5/2008 | Weitzel et al. |
| 2008/0133006 A1 | 6/2008 | Crosby et al. |
| 2008/0146996 A1 | 6/2008 | Smisson |
| 2008/0210016 A1 | 9/2008 | Zwirn et al. |
| 2008/0262289 A1 | 10/2008 | Goldowsky |
| 2008/0262361 A1 | 10/2008 | Gutfinger et al. |
| 2008/0269822 A1 | 10/2008 | Ljungstrom et al. |
| 2008/0275339 A1* | 11/2008 | Thiemann ............ A61B 8/0875 600/437 |
| 2008/0306328 A1 | 12/2008 | Ercolani |
| 2009/0024042 A1 | 1/2009 | Nunez et al. |
| 2009/0025459 A1 | 1/2009 | Zhang et al. |
| 2009/0064755 A1 | 3/2009 | Fleischli et al. |
| 2009/0105799 A1 | 4/2009 | Hekmat et al. |
| 2009/0131765 A1 | 5/2009 | Roschak et al. |
| 2009/0204163 A1 | 8/2009 | Shuros et al. |
| 2009/0226328 A1 | 9/2009 | Morello |
| 2009/0312650 A1 | 12/2009 | Maile et al. |
| 2010/0010354 A1 | 1/2010 | Skerl et al. |
| 2010/0082099 A1 | 4/2010 | Vodermayer et al. |
| 2010/0087742 A1 | 4/2010 | Bishop et al. |
| 2010/0160801 A1 | 6/2010 | Takatani et al. |
| 2010/0219967 A1 | 9/2010 | Kaufmann |
| 2010/0222632 A1 | 9/2010 | Poirier |
| 2010/0222633 A1 | 9/2010 | Poirier |
| 2010/0222635 A1 | 9/2010 | Poirier |
| 2010/0222878 A1 | 9/2010 | Poirier |
| 2010/0268017 A1 | 10/2010 | Siess |
| 2010/0298625 A1 | 11/2010 | Reichenbach et al. |
| 2010/0324378 A1 | 12/2010 | Tran et al. |
| 2011/0004075 A1 | 1/2011 | Stahmann et al. |
| 2011/0022057 A1 | 1/2011 | Eigler et al. |
| 2011/0071336 A1 | 3/2011 | Yomtov |
| 2011/0144744 A1 | 6/2011 | Wampler |
| 2011/0172505 A1 | 7/2011 | Kim |
| 2011/0184301 A1 | 7/2011 | Holmstrom |
| 2011/0218435 A1 | 9/2011 | Srinivasan et al. |
| 2011/0230068 A1 | 9/2011 | Pahl |
| 2012/0022645 A1 | 1/2012 | Burke |
| 2012/0084024 A1 | 4/2012 | Norcross, Jr. |
| 2012/0150089 A1 | 6/2012 | Penka et al. |
| 2012/0203476 A1 | 8/2012 | Dam |
| 2012/0245404 A1 | 9/2012 | Smith |
| 2012/0247200 A1 | 10/2012 | Ahonen et al. |
| 2012/0310037 A1 | 12/2012 | Choi et al. |
| 2012/0330214 A1 | 12/2012 | Peters et al. |
| 2013/0041204 A1 | 2/2013 | Heilman et al. |
| 2013/0046129 A1 | 2/2013 | Medvedev et al. |
| 2013/0066141 A1 | 3/2013 | Doerr et al. |
| 2013/0066142 A1 | 3/2013 | Doerr et al. |
| 2013/0072846 A1 | 3/2013 | Heide et al. |
| 2013/0116575 A1 | 5/2013 | Mickle et al. |
| 2013/0144379 A1 | 6/2013 | Najafi et al. |
| 2013/0289334 A1 | 10/2013 | Badstibner |
| 2013/0289376 A1 | 10/2013 | Lang |
| 2013/0303831 A1 | 11/2013 | Evans |
| 2013/0304404 A1* | 11/2013 | Dam .................. A61B 5/14535 702/54 |
| 2014/0005467 A1 | 1/2014 | Farnan et al. |
| 2014/0013852 A1 | 1/2014 | Brown et al. |
| 2014/0030122 A1 | 1/2014 | Ozaki |
| 2014/0100414 A1 | 4/2014 | Tamez et al. |
| 2014/0114202 A1 | 4/2014 | Hein et al. |
| 2014/0128659 A1 | 5/2014 | Heuring et al. |
| 2014/0200389 A1 | 7/2014 | Yanai et al. |
| 2014/0243688 A1 | 8/2014 | Caron et al. |
| 2014/0275720 A1 | 9/2014 | Ferrari |
| 2014/0275727 A1 | 9/2014 | Bonde |
| 2014/0296677 A1 | 10/2014 | McEowen |
| 2014/0303426 A1 | 10/2014 | Kerkhoffs et al. |
| 2014/0342203 A1 | 11/2014 | Elian |
| 2015/0032007 A1 | 1/2015 | Ottevanger et al. |
| 2015/0141832 A1 | 5/2015 | Yu et al. |
| 2015/0141842 A1 | 5/2015 | Spanier et al. |
| 2015/0157216 A1 | 6/2015 | Stigall et al. |
| 2015/0174307 A1 | 6/2015 | Eckman et al. |
| 2015/0190092 A1 | 7/2015 | Mori |
| 2015/0250935 A1 | 9/2015 | Anderson et al. |
| 2015/0273184 A1 | 10/2015 | Scott et al. |
| 2015/0290372 A1 | 10/2015 | Muller et al. |
| 2015/0306290 A1 | 10/2015 | Rosenberg et al. |
| 2015/0306291 A1 | 10/2015 | Bonde et al. |
| 2015/0307344 A1 | 10/2015 | Ernst |
| 2015/0327921 A1 | 11/2015 | Govari |
| 2015/0335804 A1 | 11/2015 | Marseille et al. |
| 2015/0365738 A1 | 12/2015 | Purvis et al. |
| 2016/0000983 A1 | 1/2016 | Mohl et al. |
| 2016/0008531 A1 | 1/2016 | Wang et al. |
| 2016/0022889 A1 | 1/2016 | Bluvshtein et al. |
| 2016/0022890 A1 | 1/2016 | Schwammenthal et al. |
| 2016/0045165 A1 | 2/2016 | Braido et al. |
| 2016/0095968 A1 | 4/2016 | Rudser |
| 2016/0101230 A1 | 4/2016 | Ochsner et al. |
| 2016/0144166 A1 | 5/2016 | Decré et al. |
| 2016/0151553 A1 | 6/2016 | Bonde |
| 2016/0166747 A1 | 6/2016 | Frazier et al. |
| 2016/0213828 A1 | 7/2016 | Sievers |
| 2016/0250399 A1 | 9/2016 | Tiller et al. |
| 2016/0278856 A1 | 9/2016 | Panescu |
| 2016/0302672 A1 | 10/2016 | Kuri |
| 2016/0317043 A1 | 11/2016 | Campo |
| 2016/0338629 A1 | 11/2016 | Doerr |
| 2017/0010144 A1 | 1/2017 | Lenner et al. |
| 2017/0021070 A1 | 1/2017 | Petersen |
| 2017/0049945 A1 | 2/2017 | Halvorsen et al. |
| 2017/0086780 A1 | 3/2017 | Sokulin et al. |
| 2017/0098491 A1 | 4/2017 | Ziaie et al. |
| 2017/0112985 A1 | 4/2017 | Yomtov |
| 2017/0128646 A1 | 5/2017 | Karch |
| 2017/0136164 A1 | 5/2017 | Yeatts |
| 2017/0202575 A1 | 7/2017 | Stanfield et al. |
| 2017/0224279 A1 | 8/2017 | Cahan et al. |
| 2017/0239407 A1 | 8/2017 | Hayward |
| 2017/0258980 A1 | 9/2017 | Katsuki et al. |

(56) References Cited

U.S. PATENT DOCUMENTS

| | | |
|---|---|---|
| 2017/0348470 A1 | 12/2017 | D'Ambrosio et al. |
| 2017/0354812 A1 | 12/2017 | Callaghan et al. |
| 2018/0064860 A1 | 3/2018 | Nunez et al. |
| 2018/0078159 A1 | 3/2018 | Edelman et al. |
| 2018/0093070 A1 | 4/2018 | Cottone |
| 2018/0110910 A1 | 4/2018 | Rodemerk et al. |
| 2018/0199635 A1 | 7/2018 | Longinotti-Buitoni et al. |
| 2018/0250457 A1 | 9/2018 | Morello et al. |
| 2018/0256796 A1 | 9/2018 | Hansen |
| 2018/0256800 A1 | 9/2018 | Conyers et al. |
| 2018/0264182 A1 | 9/2018 | Spanier et al. |
| 2018/0280598 A1 | 10/2018 | Curran et al. |
| 2018/0316209 A1 | 11/2018 | Gliner |
| 2018/0326131 A1 | 11/2018 | Muller et al. |
| 2018/0333059 A1 | 11/2018 | Casas |
| 2018/0353667 A1 | 12/2018 | Moyer et al. |
| 2018/0369469 A1 | 12/2018 | Le Duc De Lillers et al. |
| 2019/0001038 A1 | 1/2019 | Yomtov et al. |
| 2019/0054223 A1 | 2/2019 | Frazier et al. |
| 2019/0083690 A1 | 3/2019 | Siess et al. |
| 2019/0192752 A1 | 6/2019 | Tiller et al. |
| 2019/0192753 A1 | 6/2019 | Liu et al. |
| 2019/0209755 A1 | 7/2019 | Nix et al. |
| 2019/0209758 A1 | 7/2019 | Tuval et al. |
| 2019/0216995 A1 | 7/2019 | Kapur et al. |
| 2019/0217002 A1 | 7/2019 | Urakabe |
| 2019/0223877 A1 | 7/2019 | Nitzen et al. |
| 2019/0240680 A1 | 8/2019 | Hayakawa |
| 2019/0254543 A1 | 8/2019 | Hartholt et al. |
| 2019/0282741 A1 | 9/2019 | Franano et al. |
| 2019/0282744 A1 | 9/2019 | D'Ambrosio et al. |
| 2019/0351117 A1 | 11/2019 | Cambronne et al. |
| 2019/0351118 A1 | 11/2019 | Graichen et al. |
| 2020/0016309 A1 | 1/2020 | Kallenbach et al. |
| 2020/0038567 A1 | 2/2020 | Siess et al. |
| 2020/0060559 A1 | 2/2020 | Edelman et al. |
| 2020/0069857 A1 | 3/2020 | Schwammenthal et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0253583 A1* | 8/2020 | Brisken ............... A61B 8/4444 |
| 2020/0312450 A1 | 10/2020 | Agnello et al. |
| 2021/0268264 A1 | 9/2021 | Stotz |
| 2021/0290087 A1 | 9/2021 | Schlebusch |
| 2021/0290930 A1 | 9/2021 | Kasel |
| 2021/0290933 A1 | 9/2021 | Stotz |
| 2021/0339004 A1 | 11/2021 | Schlebusch et al. |
| 2021/0346674 A1 | 11/2021 | Baumbach et al. |
| 2021/0346675 A1 | 11/2021 | Schlebusch et al. |
| 2021/0346676 A1 | 11/2021 | Schlebusch et al. |
| 2021/0346677 A1 | 11/2021 | Baumbach et al. |
| 2021/0346678 A1 | 11/2021 | Baumbach et al. |
| 2021/0378523 A1 | 12/2021 | Budde |
| 2021/0379359 A1 | 12/2021 | Schellenberg |
| 2021/0379360 A1 | 12/2021 | Schellenberg |
| 2021/0393944 A1 | 12/2021 | Wenning |
| 2022/0016411 A1 | 1/2022 | Winterwerber |
| 2022/0032032 A1 | 2/2022 | Schlebusch et al. |
| 2022/0032036 A1 | 2/2022 | Baumbach et al. |
| 2022/0039669 A1 | 2/2022 | Schlebusch et al. |
| 2022/0047173 A1 | 2/2022 | Stotz et al. |
| 2022/0050037 A1 | 2/2022 | Stotz et al. |
| 2022/0072298 A1 | 3/2022 | Spanier et al. |
| 2022/0076807 A1 | 3/2022 | Agnello |
| 2022/0079457 A1 | 3/2022 | Tuval et al. |
| 2022/0105339 A1 | 4/2022 | Nix et al. |
| 2022/0126085 A1 | 4/2022 | Farnan |
| 2022/0126086 A1 | 4/2022 | Schlebusch et al. |
| 2022/0142462 A1 | 5/2022 | Douk et al. |
| 2022/0161019 A1 | 5/2022 | Mitze et al. |
| 2022/0361762 A1 | 11/2022 | Lalancette |
| 2023/0173250 A1 | 6/2023 | Stigloher |
| 2023/0191141 A1 | 6/2023 | Wenning et al. |
| 2024/0011808 A1 | 1/2024 | Winzer et al. |
| 2024/0074828 A1 | 3/2024 | Wenning |
| 2024/0245902 A1 | 7/2024 | Schlebusch et al. |

FOREIGN PATENT DOCUMENTS

| | | |
|---|---|---|
| CN | 1222862 A | 7/1999 |
| CN | 1202871 C | 5/2005 |
| CN | 1661338 A | 8/2005 |
| CN | 101128168 | 2/2008 |
| CN | 101208045 | 6/2008 |
| CN | 101214158 | 7/2008 |
| CN | 101351237 | 1/2009 |
| CN | 101448535 | 6/2009 |
| CN | 101460094 | 6/2009 |
| CN | 101579233 | 11/2009 |
| CN | 201437016 | 4/2010 |
| CN | 101711683 | 5/2010 |
| CN | 201658687 | 12/2010 |
| CN | 102421372 | 4/2012 |
| CN | 102803923 | 11/2012 |
| CN | 103328018 | 9/2013 |
| CN | 103857326 | 6/2014 |
| CN | 103957957 | 7/2014 |
| CN | 104105449 | 10/2014 |
| CN | 104188687 | 12/2014 |
| CN | 106104229 | 11/2016 |
| CN | 106333707 | 1/2017 |
| CN | 206007680 | 3/2017 |
| CN | 107530479 | 1/2018 |
| CN | 107632167 | 1/2018 |
| CN | 109939282 | 6/2019 |
| CN | 209790495 | 12/2019 |
| CN | 210020563 | 2/2020 |
| DE | 195 20 920 | 12/1995 |
| DE | 198 21 307 | 10/1999 |
| DE | 100 59 714 | 5/2002 |
| DE | 100 60 275 | 6/2002 |
| DE | 101 44 269 | 3/2003 |
| DE | 102 26 305 | 10/2003 |
| DE | 10 2006 001 180 | 9/2007 |
| DE | 10 2009 007 216 | 8/2010 |
| DE | 10 2009 011 726 | 9/2010 |
| DE | 10 2009 025 464 | 1/2011 |
| DE | 10 2009 047 845 | 3/2011 |
| DE | 10 2011 106 142 | 12/2012 |
| DE | 20 2011 110 389 | 9/2013 |
| DE | 10 2015 004 177 | 10/2015 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2018 208 536 | 12/2019 |
| DE | 10 2018 208 862 | 12/2019 |
| DE | 10 2018 208 916 | 12/2019 |
| DE | 10 2018 208 927 | 12/2019 |
| DE | 10 2018 208 945 | 12/2019 |
| DE | 10 2018 210 076 | 12/2019 |
| DE | 10 2018 212 153 | 1/2020 |
| DE | 10 2018 213 151 | 2/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 151 | 3/2022 |
| EP | 0 794 411 | 9/1997 |
| EP | 0 916 359 | 5/1999 |
| EP | 1 062 959 | 12/2000 |
| EP | 1 339 443 | 11/2001 |
| EP | 1 011 803 | 9/2004 |
| EP | 1 354 606 | 6/2006 |
| EP | 2 143 385 | 1/2010 |
| EP | 2 175 770 | 4/2010 |
| EP | 2 187 807 | 6/2012 |
| EP | 2 570 143 | 3/2013 |
| EP | 2 401 003 | 10/2013 |
| EP | 1 871 441 | 11/2014 |
| EP | 2 859 911 | 4/2015 |

(56) References Cited

FOREIGN PATENT DOCUMENTS

| | | |
|---|---|---|
| EP | 2 213 227 | 8/2016 |
| EP | 2 835 141 | 8/2016 |
| EP | 3 088 016 | 11/2016 |
| EP | 2 585 129 | 3/2017 |
| EP | 2 945 661 | 11/2017 |
| EP | 2 136 861 | 12/2017 |
| EP | 3 020 426 | 12/2017 |
| EP | 3 287 154 | 2/2018 |
| EP | 3 205 359 | 8/2018 |
| EP | 3 205 360 | 8/2018 |
| EP | 3 389 738 | 8/2019 |
| EP | 2 505 090 | 12/2019 |
| EP | 3 668 560 | 6/2020 |
| EP | 3 720 520 | 10/2020 |
| EP | 3 753 594 | 12/2020 |
| EP | 3 357 523 | 1/2021 |
| EP | 3 490 628 | 2/2021 |
| EP | 3 487 548 | 3/2021 |
| EP | 3 509 661 | 3/2021 |
| EP | 3 515 523 | 3/2021 |
| EP | 3 528 863 | 3/2021 |
| EP | 3 615 103 | 3/2021 |
| EP | 4 271 461 | 3/2021 |
| EP | 3 131 600 | 6/2021 |
| EP | 3 131 615 | 6/2021 |
| EP | 3 463 505 | 9/2021 |
| EP | 3 884 970 | 9/2021 |
| EP | 2 599 510 | 10/2021 |
| EP | 3 003 421 | 10/2021 |
| EP | 3 027 241 | 10/2021 |
| EP | 3 668 561 | 10/2021 |
| EP | 3 164 168 | 12/2021 |
| EP | 3 344 129 | 12/2021 |
| EP | 3 624 867 | 3/2022 |
| EP | 3 651 822 | 3/2022 |
| EP | 3 689 389 | 3/2022 |
| EP | 3 737 436 | 3/2022 |
| EP | 3 972 661 | 3/2022 |
| EP | 3 984 589 | 4/2022 |
| EP | 3 654 006 | 5/2022 |
| EP | 3 737 310 | 7/2022 |
| EP | 2 999 400 | 8/2022 |
| EP | 3 711 788 | 8/2022 |
| EP | 3 694 573 | 9/2022 |
| EP | 3 600 477 | 10/2022 |
| EP | 3 897 768 | 10/2022 |
| EP | 2 892 583 | 1/2023 |
| EP | 3 370 797 | 1/2023 |
| EP | 3 597 231 | 1/2023 |
| EP | 3 668 562 | 1/2023 |
| EP | 3 856 275 | 1/2023 |
| EP | 3 003 420 | 2/2023 |
| EP | 3 397 299 | 2/2023 |
| EP | 3 046 594 | 3/2023 |
| EP | 3 938 005 | 4/2023 |
| EP | 3 685 562 | 5/2023 |
| EP | 3 397 298 | 7/2023 |
| EP | 3 809 959 | 7/2023 |
| EP | 2 072 150 | 9/2023 |
| EP | 2 961 984 | 9/2023 |
| EP | 3 352 808 | 9/2023 |
| EP | 3 768 156 | 9/2023 |
| EP | 4 052 754 | 10/2023 |
| EP | 3 157 596 | 11/2023 |
| EP | 3 766 428 | 11/2023 |
| EP | 3 781 027 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 768 340 | 12/2023 |
| EP | 3 801 675 | 1/2024 |
| EP | 3 566 636 | 2/2024 |
| EP | 3 634 526 | 2/2024 |
| EP | 3 768 347 | 2/2024 |
| EP | 3 790 606 | 2/2024 |
| EP | 3 930 780 | 2/2024 |
| EP | 3 397 147 | 3/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 970 765 | 7/2024 |
| EP | 3 854 444 | 9/2024 |
| EP | 3 793 674 | 10/2024 |
| EP | 3 618 885 | 11/2024 |
| EP | 4 034 221 | 11/2024 |
| EP | 3 809 960 | 12/2024 |
| ES | 2 913 485 | 6/2022 |
| JP | S59-080229 | 5/1984 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-518907 | 6/2010 |
| JP | 2012-520157 | 9/2012 |
| JP | 2013-128792 | 7/2013 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 2017-176719 | 10/2017 |
| JP | 2017-532084 | 11/2017 |
| JP | 2019-523110 | 8/2019 |
| JP | 2020-072985 | 5/2020 |
| WO | WO 92/015239 | 9/1992 |
| WO | WO 98/043688 | 10/1998 |
| WO | WO 00/033047 | 6/2000 |
| WO | WO 2006/122001 | 11/2006 |
| WO | WO 2010/142286 | 12/2010 |
| WO | WO 2010/143272 | 12/2010 |
| WO | WO 2012/018917 | 2/2012 |
| WO | WO 2012/112378 | 8/2012 |
| WO | WO 2013/160443 | 10/2013 |
| WO | WO 2014/042925 | 3/2014 |
| WO | WO 2014/141284 | 9/2014 |
| WO | WO 2014/165635 | 10/2014 |
| WO | WO 2015/085220 | 6/2015 |

(56) References Cited

FOREIGN PATENT DOCUMENTS

| | | |
|---|---|---|
| WO | WO 2016/001284 | 1/2016 |
| WO | WO 2016/066180 | 5/2016 |
| WO | WO 2016/137743 | 9/2016 |
| WO | WO 2017/032751 | 3/2017 |
| WO | WO 2017/066257 | 4/2017 |
| WO | WO 2017/106190 | 6/2017 |
| WO | WO 2017/147291 | 8/2017 |
| WO | WO 2017/214118 | 12/2017 |
| WO | WO 2018/005228 | 1/2018 |
| WO | WO 2018/048800 | 3/2018 |
| WO | WO 2018/109038 | 6/2018 |
| WO | WO 2018/213089 | 11/2018 |
| WO | WO 2019/013794 | 1/2019 |
| WO | WO 2019/034670 | 2/2019 |
| WO | WO 2019/034775 | 2/2019 |
| WO | WO 2019/078723 | 4/2019 |
| WO | WO 2019/126721 | 6/2019 |
| WO | WO 2019/137911 | 7/2019 |
| WO | WO 2019/193604 | 10/2019 |
| WO | WO 2019/219883 | 11/2019 |
| WO | WO 2019/229210 | 12/2019 |
| WO | WO 2019/229220 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/243582 | 12/2019 |
| WO | WO 2020/030686 | 2/2020 |
| WO | WO 2020/030706 | 2/2020 |
| WO | WO 2020/064707 | 4/2020 |
| WO | WO 2020/089429 | 5/2020 |
| WO | WO 2020/198280 | 10/2020 |
| WO | WO 2020/243756 | 12/2020 |
| WO | WO 2022/074136 | 4/2022 |
| WO | WO 2022/109590 | 5/2022 |
| WO | WO 2022/173970 | 8/2022 |
| WO | WO 2023/049813 | 3/2023 |

OTHER PUBLICATIONS

Leguy et al., "Assessment of Blood vol. Flow in Slightly Curved Arteries from a Single Velocity Profile", Journal of Biomechanics, 2009, pp. 1664-1672.

Lombardi et al., "Flow Rate Profiler: an instrument to measure blood velocity profiles", Ultrasonics, 2001, vol. 39, pp. 143-150.

Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.

Sinha et al., "Effect of Mechanical Assistance of the Systemic Ventricle in Single Ventricle Circulation with Cavopulmonary Connection", The Journal of Throacic and Cardiovascular Surgery, Apr. 2014, vol. 147, No. 4, pp. 1271-1275.

"Understanding Hot-Wire Anemometry", Advanced Thermal Solutions, Inc., 2007, pp. 13-17.

Vieli, A., "Doppler Flow Determination", BJA: British Journal of Anaesthesia, 1988, vol. 60, pp. 107S-112S.

Yuanyuan et al., "Characteristics Analysis for Doppler Ultrasound Blood Flow Signals", China Medical Device Information, 5(1), Feb. 28, 1999, pp. 36-42.

Zhang, Dabiao et al., "Design of Microwave Velocity and Distance Monitor System", Instrument Technique and Sensor, Hebei Normal University, Apr. 25, 2004, pp. 3.

Hertz Ph.D. et al, "Ultrasonic Engineering in Heart Diagnosis", The American Journal of Cardiology, Jan. 1967, vol. 19, No. 1, pp. 6-17.

International Search Report and Written Opinion received in PCT Application No. PCT/EP2019/064803, dated Sep. 5, 2019 in 13 pages.

International Preliminary Report on Patentability and Written Opinion received in PCT Application No. PCT/EP2019/064803, dated Aug. 12, 2020 in 7 pages.

Kong et al., "A Stein Equation Approach for Solutions to the Diophantine Equations," 2010 Chinese Control and Decision Conference, Xuzhou, May 26, 2010, pp. 3024-3028.

Koseli et al., "Online Viscosity Measurement of Complex Solutions Using Ultrasound Doppler Velocimetry", Turk J Chem, Jan. 2006, vol. 30, pp. 297-305.

McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.

Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.

Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.

HeartMate 3™ Left Ventricular Assist System, Instructions for Use, Thoratec Corporation, Aug. 2017, pp. 536. [Uploaded in 3 parts].

* cited by examiner

METHOD AND SYSTEM FOR DETERMINING THE SPEED OF SOUND IN A FLUID IN THE REGION OF A CARDIAC SUPPORT SYSTEM

BACKGROUND

Field

The invention relates to a method for determining the speed of sound in a fluid in the region of an implanted vascular support system, a system for determining the speed of sound in a fluid in the region of an implanted vascular support system, and an implantable vascular support system. The invention is particularly used in (fully) implanted left heart support systems (LVAD [Left Ventricular Assist Device]).

Description of the Related Art

Knowledge of the actually circulated blood volume of a heart support system or cardiac support system is medically of great importance, in particular for regulating the (implanted) support system.

Work is therefore being done on integrating ultrasonic-based volume flow measurement technology into the support systems. An ultrasonic Doppler measurement can be used as a measurement method, wherein only a single ultrasonic transducer is required as a transmitter and receiver element, which primarily saves installation space in the implant. The flow velocity can be calculated based on the frequency shift due to the Doppler effect:

$$\Delta f = f_0 \cdot \frac{2v}{c} \cdot \cos(\alpha)$$

Where $\Delta f$ is the resulting Doppler frequency shift, $f_0$ is the frequency of the emitted ultrasound impulse, v is the flow velocity of the medium, c is the speed of sound in the medium, and $\alpha$ is the angle between the ultrasonic sound path and the main flow direction.

In a (heart) support system, v is to be determined, $\alpha$ is generally known, and $f_0$ is known. The speed of sound c is only approximately known and depends on the composition and properties of the blood. For high measurement quality, it is therefore necessary to explicitly determine the speed of sound c in the blood by measurement.

SUMMARY

The task of the invention is to specify a method and to provide a system by which the speed of sound in a fluid, in particular the speed of sound of blood in the region of an implanted vascular support system, can be determined.

This object is achieved by the method specified in claim 1 and the system specified in claim 8. Advantageous embodiments of the invention are specified in the dependent claims.

According to claim 1, a method for determining the speed of sound in a fluid in the region of an implanted vascular support system is proposed here, comprising the following steps:
a) Transmitting an ultrasonic signal by means of an ultrasonic sensor,
b) Reflecting the ultrasonic signal on at least one sound reflector, which is arranged in the field of vision of the ultrasonic sensor and at a defined distance, at least to the ultrasonic sensor or to a further sound reflector,
c) receiving the reflected ultrasonic signal,
d) determining the speed of sound in the fluid using the reflected ultrasonic signal.

The vascular support system is preferably a cardiac support system, particularly preferably a ventricular support system. The support system is regularly used to support the circulation of blood in the cardiovascular system of a human, or patient if applicable. The support system can be arranged at least partially in a blood vessel. The blood vessel is, for example, the aorta, in particular in a left heart support system, or the pulmonary trunk (Truncus pulmonalis) into the two pulmonary arteries, in particular in a right heart support system, preferably the aorta. The support system is preferably arranged at the outlet of the left ventricle of the heart or the left ventricle. The support system is particularly preferably arranged in the aortic valve position.

The method is preferably used to measure the speed of sound in blood using ultrasound in a heart support system. The method can contribute toward determining a fluid flow velocity and/or fluid volume flow from a ventricle of a heart, in particular from a (left) ventricle of a heart towards the aorta in the region of a (fully) implanted, (left) ventricular (heart) support system. The fluid is regularly blood. The speed of sound is preferably determined in a fluid flow or fluid volume flow that flows through the support system. The method advantageously makes it possible to also determine the speed of sound or speed of flow required for a (Doppler) measurement in the blood outside of the surgical scenario with high quality, in particular by the implanted support system itself.

The explicit determination of the speed of sound is in particular made possible by integrating one or more sound reflectors in the field of vision of a Doppler ultrasonic sensor of a heart support system, in particular in combination with the enhancement of an additional analysis algorithm, in particular an additional FMCW (frequency-modulated approach)-based analysis algorithm, so that the accuracy of the Doppler-based blood flow measurement is not influenced by uncertainties in the speed of sound. The solution presented here is based in particular on enhancing a vascular support system with an integrated Doppler volume flow sensor with one or more reflectors at a defined distance to the ultrasonic element, so that the speed of sound can be determined based on the geometrically defined and known travel distance between the ultrasonic element and the reflector as well as the measured pulse time of flight and/or beat frequency.

In step a), an ultrasonic signal is emitted by means of an ultrasonic sensor. For this purpose, the ultrasonic sensor preferably comprises an ultrasonic element, which, for example due to its oscillation, is designed to emit one or more ultrasonic signals. A piezo element is particularly preferred for the ultrasonic element. Furthermore, the ultrasonic sensor is preferably aligned such that an angle between the ultrasonic sound path and the main flow direction of the fluid is less than 5°. It is also advantageous if the ultrasonic sensor is designed in the manner of an ultrasonic transducer that is configured both for transmitting and receiving ultrasonic signals, for example in that an ultrasonic element can function as a transmitter and receiver element. The emitted ultrasonic signal can also be referred to as a transmission signal and generally has a specific frequency and/or amplitude. In addition, the transmission signal can also be pulsed or comprise at least an (im-)pulse (for the pulse time of flight approach). Furthermore, the transmission signal can preferably be influenced by frequency modulation, in particular for determining beat frequencies (for the FMCW approach).

In step b), the ultrasonic signal is reflected on at least one sound reflector, which is arranged in the field of vision of the ultrasonic sensor and at a (pre-)defined distance to the ultrasonic sensor and/or to further sound reflector, which is also arranged in the field of vision of the ultrasonic sensor. The field of vision of the ultrasonic sensor is usually determined or formed by its emission characteristic. The sound reflector is preferably arranged circumferentially along an inner circumference of a flow channel of the support system. The at least one sound reflector preferably projects at least partially into a flow path of the fluid or flow channel for the fluid through the support system. This flow path or channel can, for example travel through, or be formed by, a(n) (inlet) cannula. It is particularly preferred in this case that the at least one sound reflector is arranged circumferentially along a(n) (inner) surface of the cannula. This defined distance between the ultrasonic sensor and the sound reflector is preferably in the range of 5 to 35 mm, in particular 5 to 30 mm.

The at least one sound reflector can have at least one air-filled cavity. The at least one sound reflector is preferably oriented and/or aligned such that it causes (only) one reflection or (only) reflections in the direction of the ultrasonic sensor. In other words, the at least one sound reflector is oriented and/or aligned such that it reflects incident ultrasonic waves or signals in particular directly and/or only toward the ultrasonic sensor. Furthermore, the at least one sound reflector is preferably aligned such that a surface of the reflector is oriented in parallel to the incident ultrasonic wavefront. Preferably, the at least one sound reflector is a component of the support system that is separate from the further components (e.g., channel inner wall) that come into contact with the fluid. The at least one sound reflector is preferably mounted or fastened to a channel inner wall of the support system.

In step c), the reflected ultrasonic signal is received. The reflected ultrasonic signal is preferably received by means of the ultrasonic sensor. The received ultrasonic signal can also be referred to as a receiving signal. In particular if several sound reflectors are specified, several reflected ultrasound signals can also be received in step c).

In step d), the speed of sound in the fluid is determined using the reflected ultrasonic signal. For this purpose, the ultrasonic signal can be evaluated or analyzed, for example by means of an analysis unit of the support system, in particular the ultrasonic sensor. A (pulse) time of flight-based approach and/or a so-called FMCW-based approach can be performed in this case.

According to an advantageous embodiment, it is proposed that the ultrasonic signal is reflected on at least two sound reflectors, which are arranged at different distances from the ultrasonic sensor. The two sound reflectors generally have a (pre-)defined distance to each other. This distance is preferably in the range of 1 to 10 mm. By using at least two reflectors at different distances, the accuracy can be advantageously further increased, in particular because uncertainties in the speed of sound of the impedance adjustment layer of the ultrasonic transducer and tissue deposits potentially present thereon can be compensated.

According to an advantageous embodiment, it is proposed that the at least one sound reflector has an acoustic impedance that is greater than the largest acoustic impedance of the fluid or is less than the lowest acoustic impedance of the fluid. The at least one sound reflector preferably has an acoustic impedance that differs by at least 5 MRayl from the acoustic impedance of the fluid. If several sound reflectors are specified, they can have the same acoustic impedance or acoustic impedances that differ from each other. However, all present sound reflectors should have an acoustic impedance that is respectively greater than the largest acoustic impedance of the fluid or less than the lowest acoustic impedance of the fluid. Furthermore, the at least one sound reflector preferably has an acoustic impedance in the range of 2 to 80 MRayl. Furthermore, the at least one sound reflector is preferably formed using one or more of the following materials: Titanium, medical stainless steel, e.g., MP35N, platinum iridium, NiTiNol.

Furthermore, the at least one sound reflector preferably has a reflection factor that is greater than the largest reflection factor of the fluid. A reflection factor of the sound reflector in this case is in particular defined as the reflection factor of the boundary layer between the material of the sound reflector and the fluid. A reflection factor of the fluid is in particular defined as the reflection factor of the boundary layer between blood cells and blood serum. If several sound reflectors are specified, they can have the same reflection factor or reflection factors that differ from each other. However, all present sound reflectors should have a reflection factor that is respectively greater than the largest reflection factor of the fluid. The reflection factor of the at least one sound reflector is preferably in the range of 0.3 to 0.99.

According to an advantageous embodiment, it is proposed that the at least one sound reflector be embedded in an embedding material. The embedding material preferably has an acoustic impedance that essentially corresponds to the acoustic impedance of the fluid. For example, a silicone can be used as the embedding material. Further preferably, the embedding material at least partially, preferably completely, envelops the surface of the sound reflector facing toward the fluid. In particular, the at least one sound reflector (using the embedding material) is preferably embedded in a planar and/or smooth surface. Preferably, the at least one sound reflector (by means of the embedding material) is embedded into a surface, the maximum slope of which is less than the maximum slope of the exterior surface of the sound reflector.

According to an advantageous embodiment, it is proposed that the speed of sound be determined using a (pulse) time of flight-based analysis algorithm. In other words, this means, in particular, that a (pulse) time of flight-based analysis algorithm is used to determine the speed of sound. The pulse-time-based analysis algorithm preferably determines the speed of sound as a function of the defined distance at least between the ultrasonic sensor and the sound reflector or between two sound reflectors and at least one (measured) signal time of flight. Particularly preferably, the signal time(s) of flight is/are determined based on a cross-correlation, in particular between the transmission pulse (pulse of the emitted ultrasonic signal) and the received pulses delayed by the time(s) of flight and reflected on the sound reflectors (pulse of the received, reflected ultrasonic signals).

According to an advantageous embodiment, it is proposed that the speed of sound be determined using an FMCW-based analysis algorithm. In other words, this means in particular that an FMCW-based analysis algorithm is used to determine the speed of sound. FMCW is an acronym for frequency modulated continuous wave.

The FMCW-based analysis algorithm preferably determines the speed of sound as a function of the defined distance at least between the ultrasonic sensor and the sound reflector or between two sound reflectors, a change in a frequency of an ultrasonic signal, and at least one (resulting) beat frequency. Particularly preferably, the speed of sound is determined as a function of the defined distance between the ultrasonic sensor and the sound-reflector and/or between two sound reflectors, the slope of a frequency ramp and at least one (resulting) beat frequency.

Preferably, a beat frequency is determined by and/or for the FMCW-based analysis algorithm. The beat frequency can also be referred to as the differential frequency and/or beat frequency. The beat frequency is advantageously determined from an overlay of the ultrasonic signal (transmitted signal) emitted by the ultrasonic sensor with the reflected ultrasonic signal (receiving signal) received by the ultrasonic sensor. As a rule, the number of beat frequencies determined or to be determined corresponds to the number of (ultra)sonic reflectors. Furthermore, a discrete Fourier transformation (DFT) or fast Fourier transformation (FFT) can preferably be used to determine the beat frequency.

According to a further aspect, a system for determining the speed of sound in a fluid in the region of an implanted vascular support system is proposed, comprising:
 an ultrasonic sensor that is arranged in or on the support system,
 at least one sound reflector that is arranged in the field of vision of the ultrasonic sensor and at a defined distance at least to the ultrasonic sensor or to a further sound reflector.

According to an advantageous embodiment, it is proposed that at least two sound reflectors be arranged at different distances to the ultrasonic sensor. Furthermore, it is also preferred for the system that the at least one sound reflector be embedded into an embedding material.

According to an advantageous embodiment, it is proposed that an analysis unit is specified in which a pulse-time-based analysis algorithm is stored. Alternatively or cumulatively, an analysis unit can be specified in which an FMCW-based analysis algorithm is stored. The analysis unit is preferably a component of the support system, in particular of the ultrasonic sensor. Furthermore, the analysis unit is preferably configured to execute a method proposed herein. The analysis unit can have a memory in which the pulse time of flight-based analysis algorithm and/or the FMCW-based analysis algorithm is or are stored. In addition, the analysis unit can comprise a microprocessor that can access the memory. The processing unit preferably receives data from an ultrasonic element of the ultrasonic sensor.

According to a further aspect, an implantable vascular support system is proposed, comprising a system proposed herein for determining the speed of sound. The support system is preferably a left ventricular heart support system (LVAD) or a percutaneous, minimally invasive left heart support system. Furthermore, it is preferred that said system can be fully implanted. In other words, this means in particular that the support system is completely in the patient's body and remains there. The support system is particularly preferably configured and/or suitable such that it can be arranged at least partially in a ventricle, preferably the left ventricle of a heart and/or aorta, in particular in an aortic valve position.

Furthermore, the support system preferably comprises a cannula, in particular an inlet cannula and a flow machine, such as a pump. The support system can furthermore comprise an electric motor that is in this case regularly a component of the flow machine. The (inlet) cannula is preferably configured such that it can in the implanted state convey fluid from a (left) ventricle of a heart to the flow machine. The support system is preferably elongated and/or has a hose-like shape. The inlet cannula and the flow machine are preferably arranged in the region of opposite ends of the support system.

The details, features and advantageous embodiments discussed in connection with the method can also occur accordingly in the system and/or the support system presented here and vice versa. In this respect, reference is made in full to the related discussion regarding the detailed characterization of the features.

BRIEF DESCRIPTION OF THE DRAWINGS

The solution presented herein as well as its technical environment are explained below in more detail based on the figures. It is important to note that the invention is not limited by the shown exemplary embodiments. In particular, unless explicitly stated otherwise, it is also possible to extract partial aspects of the facts explained in the figures, and to combine said partial aspects with other components and/or findings from other figures and/or the present description. The following figures show schematically.

DETAILED DESCRIPTION

Figure 1:
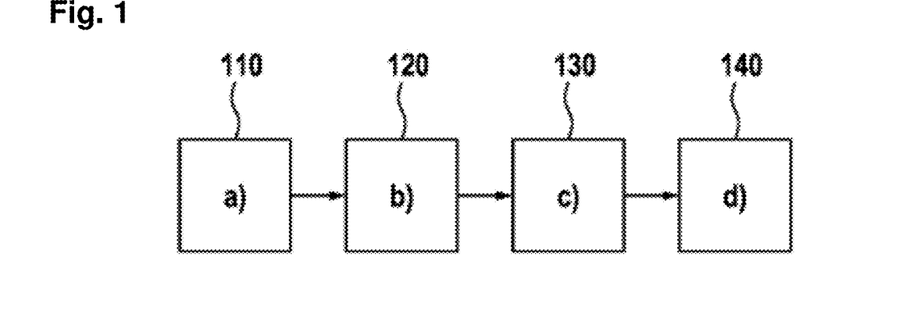
FIG. 1 a sequence of a method presented here in a standard operating sequence.

FIG. 1 shows a schematic representation of a sequence of a method presented here in a standard operating sequence. The illustrated sequence of the method steps a), b), c) and d) with the blocks 110, 120, 130 and 140 is only, exemplary. In block 110, an ultrasonic signal is transmitted with an ultrasonic sensor. In block 120, the ultrasonic signal is reflected on at least one sound reflector, which is arranged in the field of vision of the ultrasonic sensor and at a defined distance from the ultrasonic sensor. In block 130, the reflected ultrasonic signal is received. In block 140, the speed of sound is determined in the fluid using the reflected ultrasonic signal.

In particular, the method steps a), b), and c) can also be executed at least partially or simultaneously in parallel.

Figure 2A:
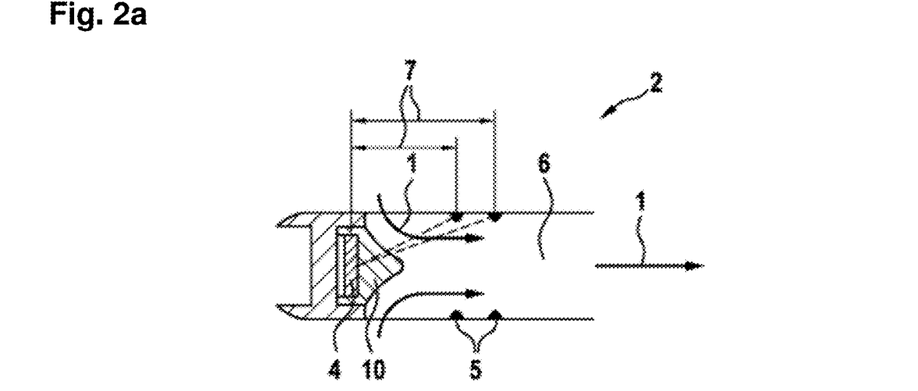
FIG. 2a a detailed view of an implantable vascular support system.
Figure 2B:
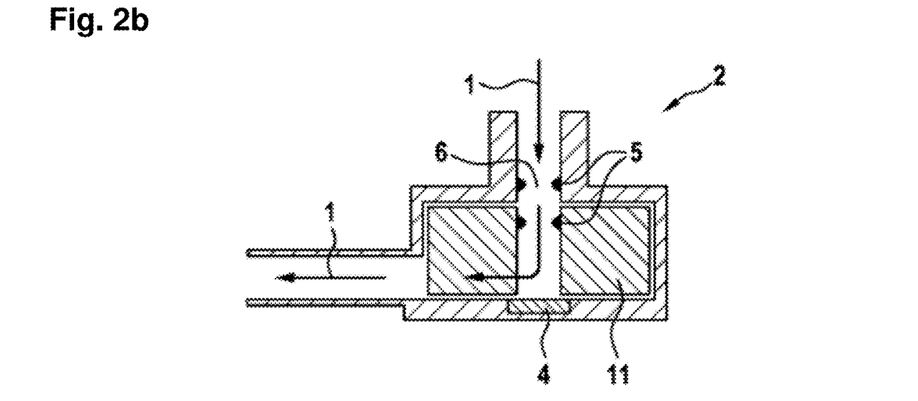
FIG. 2b a detailed view of a further implantable vascular support system.

FIG. 2a schematically shows a detailed view of an implantable vascular support system 2. FIG. 2b shows a schematic representation of a detailed view of a further implantable vascular support system 2. FIGS. 2a and 2b are explained jointly below. The reference symbols are used uniformly.

The method presented here can in principle be integrated into all designs of cardiac support systems. By way of example, FIG. 2a shows the integration into a left ventricular microaxial pump in the aortic valve position, and FIG. 2b shows the integration into an apically positioned radial support system 2.

The flow direction of the fluid 1 is represented in FIGS. 2a and 2b by arrows. In each case, an ultrasonic sensor 4 is specified, which is arranged in or on the support system 2. The ultrasonic sensors 4 are designed as an ultrasonic transducer in FIGS. 2a and 2b by way of example. In addition, two circumferential sound reflectors 5 are specified along an inner circumference of a flow channel of the support system 2, which are arranged in the field of vision 6 of the ultrasonic sensor 4 and each at a defined distance 7 to the ultrasonic sensor 4. In particular in the embodiment according to FIG. 2a, the flow channel can be formed in the interior of a(n) (inlet) cannula (not shown here) of the support system 2.

The detailed view according to FIG. 2a shows a tip of a support system 2 with a microaxial pump (not shown here); said tip accommodating the ultrasonic sensor 4. A flow conductive body 10 is in this case by way of example placed directly in front of the ultrasonic sensor 4. Said flow conductive body 10 is not spaced at a distance from the ultrasonic sensor 4 and is permeable for ultrasonic signals. The fluid 1 in this case flows in the direction of the pump. The tip of the support system 2 shown in the detailed view according to FIG. 2a can in a preferred arrangement protrude into a ventricle (not shown here) of a heart with the end shown herein on the left, wherein the pump can be arranged at least partially in the aorta (not shown here). In this arrangement, the support system thus penetrates an aortic valve (not shown here).

The detailed view according to FIG. 2b relates to a support system 2, which is also referred to as an apical radial pump. The support system 2 comprises a flow machine 11 (a pump in this case), which expels the fluid 1 as shown in radial direction.

In both exemplary pump variants, the ultrasonic sensor 4, in particular an ultrasonic element of the ultrasonic sensor 4, is usually placed such that the angle to the flow is $\alpha=0°$ (zero degrees); a best possible Doppler shift can therefore be realized.

Figure 3:
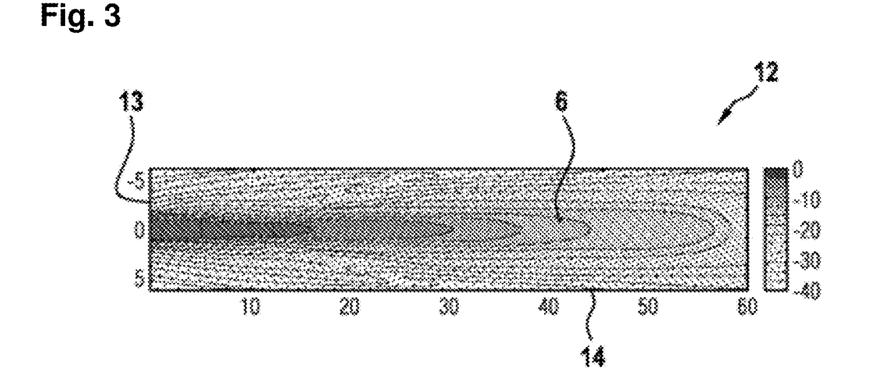
FIG. 3 an emission characteristic of an ultrasonic element.

FIG. 3 shows a schematic representation of an emission characteristic 12 of an ultrasonic element (not shown here). The emission characteristic 12 of an ultrasonic sensor or an ultrasonic element of the ultrasonic sensor is generally lobe-shaped with a main beam direction straight ahead. This is shown in FIG. 3 as an example for a circular disk ultrasonic transducer with a diameter of 3 mm at $f_0=4$ MHz. In other words, FIG. 3 illustrates the field of vision 6 of the ultrasonic sensor (not shown here). A field of vision width 13 can be measured along the ordinate (y-axis) and a field of vision length 14 can be measured along the abscissa (x-axis).

Figure 4:
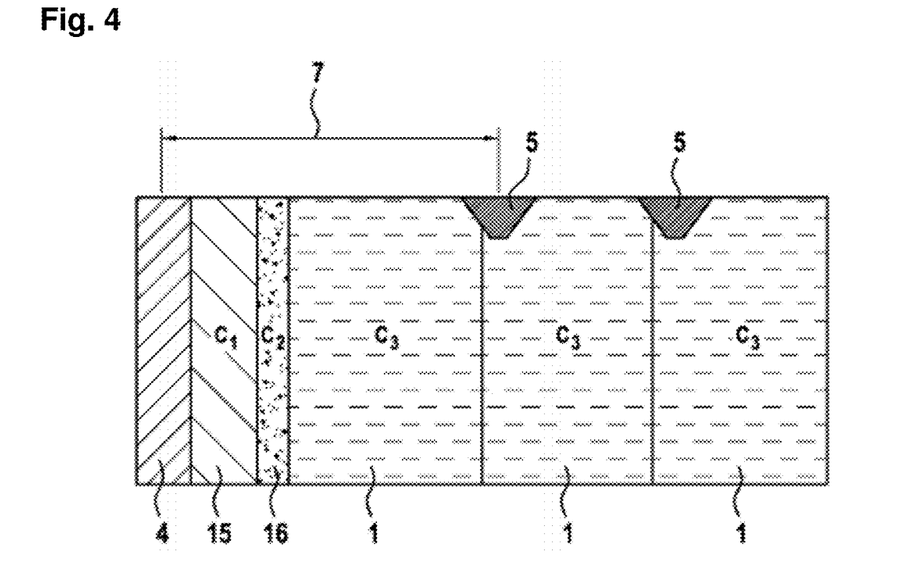
FIG. 4 an illustration of a system presented here.

FIG. 4 shows a schematic illustration of a system presented herein. The system comprises an ultrasonic sensor 4 and two sound reflectors 5, which are arranged at a different (defined) distance 7 to the ultrasonic sensor 4. The reflectors 5 project into the fluid 1 by way of example.

Each boundary layer between two acoustic impedances has a reflection factor at which a part of the sound energy is reflected according to the parameter $\Gamma$.

$$\Gamma = \frac{Z_{w2} - Z_{w1}}{Z_{w2} + Z_{w1}} |\Gamma| \leq 1$$

In this case, $Z_{w1}$ is the wave impedance before the step point and $Z_{w2}$ is the wave impedance after the step point.

The slightly different acoustic impedance of red blood cells and blood serum, for example, provides the reflected signal, which is usually used to calculate the Doppler frequency shift, from which the flow speed of the blood can be determined.

A(n) (additional) reflector proposed here should preferably have the highest possible reflection factor, which can be achieved in particular by an impedance mismatch with the blood, i.e., the acoustic impedance of the reflector should differ as clearly as possible from the blood, for example by the reflector being made of an air-filled cavity or a metal.

The method with only one reflector 5 can be faulty as soon as more than one unknown medium is present between the ultrasonic sensor 4 and the reflector 5. For example, the acoustic impedance (formula symbol: $Z_{W1}$) and thus the speed of sound (formula symbol: $C_1$) of the adjustment layers 15 could change over the years due to water diffusion, or deposits 16 of cell layers (with their own acoustic impedance $Z_{W2}$ and speed of sound $C_2$) could occur on the ultrasonic sensor 4, thus creating an additional material layer of unknown thickness and/or unknown speed of sound, as shown in greater detail in FIG. 4. In this context, the different speeds of sound of the different media are shown in FIG. 4 by way of example, namely the speed of sound $C_1$ of the adjustment layers 15, the speed of sound $C_2$ of the deposits 16 and the speed of sound $C_3$ of the fluid 1 (here: blood).

Figure 5:
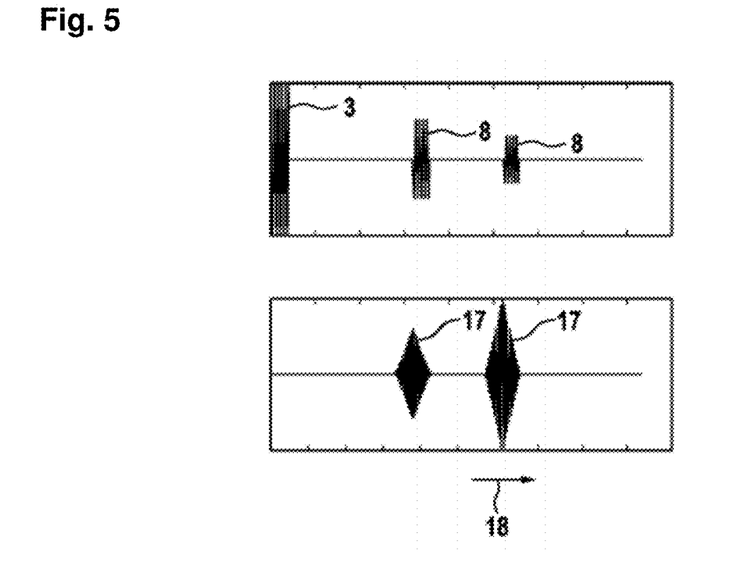
FIG. 5 an illustration of a pulse time of flight-based approach that can be used here, FIG. 6 an illustration of an FMCW-based approach that can be used here, FIG. 7 example graphs of real parts of impedances, FIG. 8a a detailed view of a system presented here, and FIG. 8b a detailed view of a further system presented here.

FIG. 5 shows a schematic illustration of a pulse time of flight-based approach usable herein. In order to explain the illustration according to FIG. 5 and/or the pulse time of flight-based approach, reference is also made to the illustration of the system according to FIG. 4.

In addition to the ultrasonic power reflected continuously by each scatter particle of fluid 1 (here: blood; in particular at the respective boundary from blood serum to blood cells), there are clear echoes at the reflectors 5, which can be identified in the received amplitude-time data. In addition, the impulse time of flight from the ultrasonic sensor 4 to the reflector 5 and back to the ultrasonic sensor 4 can be calculated. Since the mechanical design of the (heart) support system 2 and thus the (defined) distance 7 between the ultrasonic sensor 4 and reflector 5 is known, the desired speed of sound c is determined with the formula $$c = \frac{2s}{t}$$

where s is the known (defined) distance 7 between the ultrasonic sensor 4 and reflector 5 and t is the measured signal time of flight.

When using two reflectors 5 with different distances 7, as shown in FIG. 4, the time of flight $t_{R1}$ of the impulse scattered on the first reflector 5 is therefore $$t_{R1} = 2\left[\frac{s_1}{c_1} + \frac{s_2}{c_2} + \frac{s_3}{c_3}\right]$$

And the time of flight $t_{R2}$ of the pulse scattered on the second reflector 5 is $$t_{R2} = 2\left[\frac{s_1}{c_1} + \frac{s_2}{c_2} + \frac{s_3}{c_3} + \frac{s_4}{c_3}\right]$$

where $s_1$ is the thickness of the adjustment layers 15, $s_2$ is the thickness of the deposits 16, $s_3$ is the distance between deposits 16 and the first (left) reflector 5 and $s_4$ is the distance between the first (left) reflector 5 and the second (right) reflector 5, and where $c_1$ is the speed of sound in the adjustment layers 15, $c_2$ is the speed of sound in the deposits 16, and $c_3$ is the speed of sound in the fluid 1 (here: blood).

Since the adjustment layers 15 with the speed of sound $c_1$ and the deposits 16 with the speed of sound $c_2$ act equally on both impulses, the difference of the signal times of flight $t_{R2}$-$t_{R1}$ only contains components in the sought (fluid) range or in the (fluid) range relevant here with the (sought) speed of sound $c_3$:

$$t_{R2} - t_{R1} = 2\left[\frac{s_1}{c_1} + \frac{s_2}{c_2} + \frac{s_3}{c_3} + \frac{s_4}{c_3}\right] - 2\left[\frac{s_1}{c_1} + \frac{s_2}{c_2} + \frac{s_3}{c_3}\right] = 2\frac{s_4}{c_3}$$

Since the distance $s_4$ of the two reflectors 5 to one another is known, the speed of sound $c_3$ can be determined independent of the influence of additional layers between the ultrasonic sensor 4 and the reflector 5.

One possibility for determining the times of flight $t_{R1}$ and $t_{R2}$ or $t_{R1}$-$t_{R2}$ is the calculation of the cross-correlation 17 of the transmission pulse 3 (pulse of the transmitted ultrasonic signal 3) to the receiving pulses 8 (pulses of the received and reflected ultrasonic signals 8) reflected on the ultrasonic reflectors 5 and delayed by the times of flight $t_{R1}$ or $t_{R2}$. The time-discrete cross correlation 17 can be calculated as follows for an energy signal:

$$R_{xy}[n] = (x*y)[n] = \sum_{m=-\infty}^{\infty} x^*[m]y[m+n]$$

where $R_{xy}[n]$ is the discrete cross-correlation at time n, and the operator "star" as an acronym for the cross-correlation, $x^*[m]$ is the conjugated complex transmission signal over all time shifts m, and $y[m+n]$ is the receiving signal at time n over all time shifts m.

The illustration according to FIG. 5 shows an example of the result of this calculation. FIG. 5 shows the pulse of the emitted ultrasonic signal 3, the pulses of the received reflected ultrasonic signals 8 and the (time-discrete) cross correlation 17 overtime 18. The time interval $t_{R1}$-$t_{R2}$ can be determined from the distance between, e.g., the two tips (peaks) in the cross-correlation signal 17—after reverse-recalculating the discrete time steps.

Figure 6:
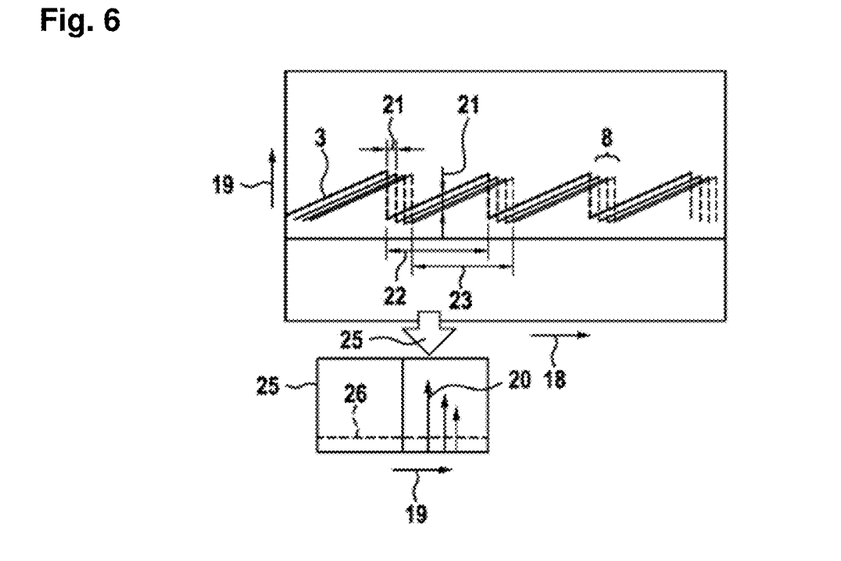

FIG. 6 shows a schematic illustration of an FMCW-based approach usable here. In order to explain the illustration according to FIG. 6 or the FMCW-based approach, reference is also made to the illustration of the system according to FIG. 4.

The (ultra)sound reflectors 5 represent the dominant targets in the emission range of the ultrasonic sensor 4, in particular due to their high reflection factor. Their beat frequencies can therefore be clearly detected in the calculated spectrum. Since the mechanical design of the (heart) support system and thus the distance between the ultrasonic sensor 4 and the reflector 5 (formula symbol x) is known, the desired speed of sound c is determined by the formula $$c = 2 * s_x * \frac{\left(\frac{bw}{T}\right)}{f_{beat,x}}$$

where $s_x$ is the known distance between the ultrasonic sensor and reflector x, bw/T is the slope of the frequency ramp, and $f_{beat,x}$ is the resulting beat frequency in the base band. In particular, since the reflectors 5 are installed in a fixed location, the resulting beat frequency is only influenced by their distance to the ultrasonic sensor 4 and the corresponding time of flight of the frequency ramp in the fluid (here: blood), and in particular contains no speed-dependent portion.

When using two reflectors 5 with different distances 7, as shown in FIG. 4, the beat frequency $f_{beat,R1}$ of the frequency ramp reflected at the first reflector is therefore $$f_{beat,R1} = 2\left(\frac{bw}{T}\right)\left[\frac{s_1}{c_1} + \frac{s_2}{c_2} + \frac{s_3}{c_3}\right]$$

and the beat frequency $f_{beat,R2}$ of the frequency reflected on the second reflector is $$f_{beat,R2} = 2\left(\frac{bw}{T}\right)\left[\frac{s_1}{c_1} + \frac{s_2}{c_2} + \frac{s_3}{c_3} + \frac{s_4}{c_3}\right]$$

where $s_1$ is the thickness of the adjustment layers 15, $s_2$ is the thickness of the deposits 16, $s_3$ is the distance between deposits 16 and the first (left) reflector 5 and $s_4$ is the distance between the first (left) reflector 5 and the second (right) reflector 5, and where $c_1$ is the speed of sound in the adjustment layers 15, $c_2$ is the speed of sound in the deposits 16, and $c_3$ is the speed of sound in the fluid 1 (here: blood).

Since the adjustment layers 15 with the speed of sound $c_1$ and the deposits 16 with the speed of sound $c_2$ act equally on both frequency ramps, the difference of the beat frequencies $f_{beat,R2}$-$f_{beat,R1}$ only contains components in the searched (fluid) range or in the (fluid) range relevant here with the (searched) speed of sound $c_3$:

$$f_{beat,R2} - f_{beat,R1} =$$
$$2\left(\frac{bw}{T}\right)\left[\frac{s_1}{c_1} + \frac{s_2}{c_2} + \frac{s_3}{c_3} + \frac{s_4}{c_3}\right] - 2\left(\frac{bw}{T}\right)\left[\frac{s_1}{c_1} + \frac{s_2}{c_2} + \frac{s_3}{c_3}\right] = 2\left(\frac{bw}{T}\right)\frac{s_4}{c_3}$$

Since the distance $s_4$ of the two reflectors 5 to one another is known, the speed of sound $c_3$ can be determined irrespective of the influence of additional layers between the ultrasonic sensor 4 and the reflector 5.

To determine the beat frequencies, the ultrasonic frequency $f_0$ is influenced by frequency modulation as an example. Without limitation, sine-wave-shaped, saw-tooth-shaped, triangular or rectangular modulation types can be used. It is particularly preferred that the ultrasonic sensor or the ultrasonic element of the sensor provide a broadband resonance and that the ramp time of flight (formula symbol: T) is much greater than the time of flight of the frequency ramps to the ultrasonic sensor 4 (ultrasound transducer) to the (ultra)-sound reflectors 5 and back again. The echoes of the successively emitted, modulated ultrasonic frequency reflected at the reflectors 5 are overlaid with the instantaneous transmission frequency ramp. The base band signal generated in this way contains the beat frequencies to be determined. These are converted by the transformation into the frequency range, e.g., by discrete Fourier transformation (DFT) or fast Fourier transformation (FFT).

The illustration according to FIG. 6 shows a possible realization of the previously described FMCW-based approach by means of a sawtooth modulation. The upper diagram of FIG. 6 shows the graph of the frequency 19 versus time 18. It can be seen that both the ultrasonic signal 3 (transmission signal) emitted by the ultrasonic sensor and the reflected ultrasonic signals 8 (receiving signals) received by the ultrasonic sensor (three here as an example) are shaped in the manner of a sawtooth. In this case, three receiving signals 8 shifted relative to the transmission signal 3 and to one another are applied as examples, which would for example be the case if three ultrasonic reflectors arranged at different distances to the ultrasonic sensor were used.

The FMCW approach regularly works with a periodic frequency modulation, in this case periodic sawtooth modulation, which should be as time-linear as possible to ensure the best-possible accuracy of the measurement. The modulation is usually performed cyclically. Such a cycle from the lowest to the highest frequency is also referred to as a signal burst. The duration of a corresponding cycle is shown in the upper diagram of FIG. 6 as a so-called chirp duration 22. In addition, a usable chirp duration 23 is marked.

The ultrasonic sensor in this case sends an example of a linear frequency-modulated signal with a sawtooth-shaped change of the transmission frequency 3. The same signal is received by the ultrasonic sensor after a reflection on one of the ultrasonic reflectors. The received signal 8 differs in the time, wherein the time difference 21 between the frequency shifts is generally proportional to the distance of the reflective ultrasonic reflector from the ultrasonic sensor. At the same time (assuming a linear frequency change), the difference frequency 20 between the transmission signal 3 and the receiving signal 8 is the same at any point in time and is thus also a measure for the distance to the reflective ultrasound reflector. This frequency difference can be evaluated in particular in the frequency range.

The frequency plots of the upper diagram in FIG. 6 are in this example used to generate a frequency spectrum 25 by overlaying/multiplying with the instantaneous transmission signal and by means of a subsequent fast Fourier transformation 24, wherein said frequency spectrum 25 carries the difference frequencies 20 in addition to the background noise 26. In a simplified manner, the receiving signal is multiplied with the instantaneous transmission signal, followed by a Fourier transformation of the base band time signal, from which the difference frequencies 20 result, which are also referred to herein as beat frequencies. The minimum range resolution of FMCW systems is $$\Delta r = \frac{c}{2 * bw} = s_4$$

is defined. Accordingly, when two ultrasonic reflectors 5 are, e.g., placed at a distance of $A_r=s_4=6$ mm to each other, and at a(n) (expected) speed of sound in blood c of about 1540 m/s (used to determine the approximately required or particularly advantageous bandwidth), it is possible to work with a bandwidth bw≈128 kHz≤150 kHz.

But a significantly higher range accuracy can be achieved by the additional use of techniques, such as the so-called zero padding (concatenating or padding of zeros) or high-performance frequency estimation methods. This can contribute to a significantly more precise determination of the speed of sound c in the blood. The achievable accuracy depends in particular on the frequency estimation method and/or the signal-to-noise ratio.

Figure 7:
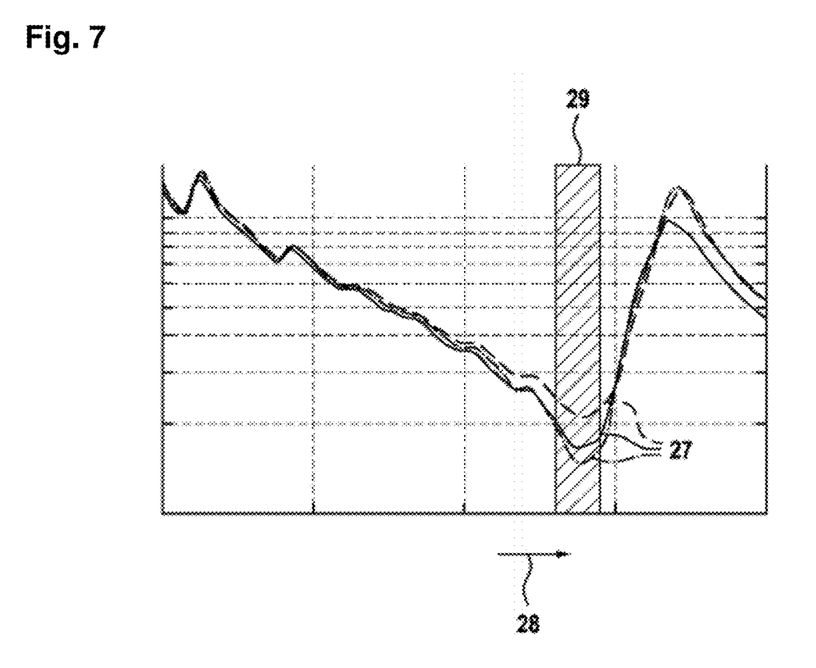

The particularly advantageous linearity can in particular be achieved over the desired frequency band when using piezo elements (as ultrasonic elements), preferably when the quality of the resonance (wide-band resonance) is reduced by backing (amplification). The illustration according to FIG. 7 shows example plots of real components 27 of the impedances of 8 MHz piezo elements versus the stimulation frequency 28. In the case shown, a frequency ramp with the example bandwidth bw=150 kHz could be placed in the frequency band 29 highlighted in gray.

Figure 8A:
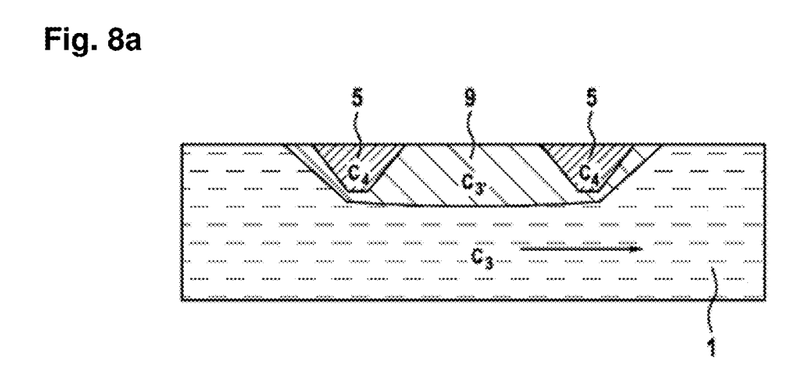
Figure 8B:
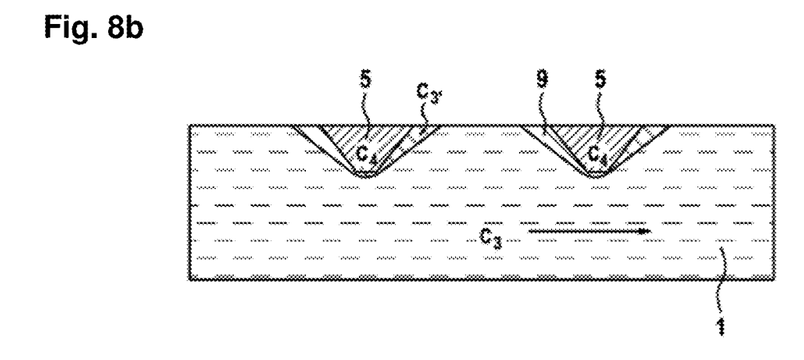

FIG. 8a shows a schematic of a detailed view of a system presented here. FIG. 8b shows a schematic of a detailed view of a further system presented here. FIGS. 8a and 8b are explained jointly below. The reference symbols are used uniformly.

To achieve the best possible reflection, the surface of the reflector should be parallel to the incident ultrasonic wavefront. Since non-planar surfaces such as superimposed reflectors can lead to turbulence in the flow (disadvantageous for Doppler ultrasonic measurement), to the formation of thrombi, and to additional blood damage (hemolysis) due to shear forces, it is expedient to embed the reflectors 5 into an embedding material 9, as illustrated by way of example in FIGS. 8a and 8b. The embedding material 9 is used here as an example for providing a smoother surface or a surface without corners and/or edges in comparison to the reflector surface. It is particularly preferred to embed the at least one reflector 5 into a planar surface, in particular by means of the embedding material 9. The embedding material 9 should as much as possible have the same acoustic impedance as the fluid 1 (here: blood) and be as thin as possible, so that there are no additional reflections or diffractions of the acoustic impulse, unless this additional diffraction is desired. For example, the (or each) reflector 5 with an acoustic impedance $C_4$ can be embedded into a silicone with an acoustic impedance $C_{3'}$, wherein $C_{3'}$ is similar to the acoustic impedance $C_3$ of blood.

The solution presented here in particular has one or more of the following advantages:
  By supplementing at least one ultrasonic reflector in the emission range of the ultrasonic system, the speed of sound can be determined from the resulting pulse time of flight and/or the ramp time of flight from the reflector.
  The known speed of sound increases the measurement accuracy of the flow measurement.
  The speed of sound depends on the composition of the blood and can in this case be determined and used directly.
  The FMCW approach does not require a very precise time difference to be measured; an equivalent frequency difference can be determined instead, which significantly reduces the technical effort.

The invention claimed is:

1. A method for determining speed of sound in blood within a cannula of a cardiac support system, the method comprising:
  transmitting blood through the cannula of the cardiac support system via a pump of the cardiac support system;
  sending an ultrasonic signal by means of an ultrasonic sensor, the ultrasonic sensor arranged within a flow path of the blood in the cannula of the cardiac support system;

reflecting the ultrasonic signal on a first sound reflector and a second sound reflector protruding at least partially into the flow path of the blood in the cannula of the cardiac support system, the first sound reflector and second sound reflector being located in a field of vision of the ultrasonic sensor, the first sound reflector and second sound reflector located at different linear distances from the ultrasonic sensor along the flow path of the blood in the cannula;

receiving a first reflected ultrasound signal and a second reflected ultrasonic signal corresponding to the ultrasonic signal after reflection at the first sound reflector and second sound reflector respectively; and determining a speed of sound in the blood based on the first reflected ultrasonic signal and second reflected ultrasonic signal and the different linear distances.

2. The method of claim 1, wherein at least one of the first sound reflector and second sound reflector has an acoustic impedance greater than the largest acoustic impedance of the blood or less than the lowest acoustic impedance of the blood.

3. The method of claim 1, wherein at least one of the first sound reflector and second sound reflector is configured to be embedded into an embedding material.

4. The method of claim 1, wherein the speed of sound is determined based on a pulse time of flight-based analysis algorithm.

5. The method of claim 1, wherein the speed of sound is determined based on a Frequency Modulated Continuous Wave (FMCW) based analysis algorithm.

6. The method of claim 5, wherein a beat frequency is determined.

7. The method of claim 1, wherein at least one of the first sound reflector and second sound reflector is configured to project sound at least partially into a flow path of the blood formed by an inlet cannula.

8. The method of claim 1, wherein the ultrasonic signal is configured to travel along an ultrasonic sound path towards the first sound reflector and second sound reflector and the method further comprises: determining a flow velocity of the fluid within a region of the cardiac support system based on a Doppler frequency shift comprising:

$$\Delta f = f_0 \cdot 2v/c \cdot \cos(\alpha)$$

wherein $\Delta f$ is the Doppler frequency shift, $f_0$ is a frequency of the ultrasonic signal, v is the flow velocity of the fluid, c is the speed of sound in the fluid, and $\alpha$ is an angle between the ultrasonic sound path and the flow path of the fluid.

9. The method of claim 1, wherein the ultrasonic sensor is positioned downstream of the first sound reflector and the second sound reflector.

10. A system for determining speed of sound in blood within a cannula of a cardiac support system, the system comprising:

an ultrasonic sensor, which is arranged in a flow path of blood in the cannula of the cardiac support system; and at least two sound reflectors, the at least two sound reflectors protruding at least partially into the flow path of the blood in the cannula of the cardiac support system, the at least two sound reflectors located in a field of vision of the ultrasonic sensor, wherein the at least two sound reflectors comprise a first sound reflector and a second sound reflector, the first sound reflector and second sound reflector located at different linear distances from the ultrasonic sensor along the flow path of the blood in the cannula.

11. The system of claim 10, wherein each of the at least two sound reflectors is embedded into an embedding material.

12. The system of claim 10, comprising an analysis unit configured to store a pulse time of flight-based analysis algorithm.

13. The system of claim 10, comprising an analysis unit configured to store a Frequency Modulated Continuous Wave (FMCW) based analysis algorithm.

14. The system of claim 10, wherein each of the at least two sound reflectors is configured to project sound at least partially into a flow path of the blood formed by an inlet cannula.

15. The system of claim 10, wherein the ultrasonic sensor is positioned downstream of the first sound reflector and the second sound reflector.

16. A cardiac support system comprising:

an ultrasonic sensor, which is arranged within a flow path of blood in a cannula of the support system; and at least two sound reflectors protruding at least partially into the flow path of the blood in the cannula of the cardiac support system, the at least two sound reflectors located in a field of vision of the ultrasonic sensor and wherein the at least two sound reflectors comprise a first sound reflector and a second sound reflector, the first sound reflector and second sound reflector located at different linear distances from the ultrasonic sensor along the flow path of the blood.

17. The system of claim 16, wherein each of the at least two sound reflectors is configured to project sound at least partially into a flow path of the blood formed by an inlet cannula.

18. The system of claim 16, wherein the ultrasonic sensor is positioned downstream of the first sound reflector and the second sound reflector.

* * * * *

UNITED STATES PATENT AND TRADEMARK OFFICE
CERTIFICATE OF CORRECTION

PATENT NO. : 12,311,160 B2
APPLICATION NO. : 15/734322
DATED : May 27, 2025
INVENTOR(S) : Schlebusch et al.

Page 1 of 1

It is certified that error appears in the above-identified patent and that said Letters Patent is hereby corrected as shown below:

On the Title Page

Page 7, Column 2 (Other Publications), Line 7, delete "of Throacic and" and insert -- of Thoracic and --.

In the Specification

Column 2, Line 25, delete "is regularly blood." and insert -- is regular blood. --.

Column 2, Line nos. 38-39, delete "FMCW (frequency-modulated approach)-based" and insert -- FMCW (Frequency-Modulated Continuous Wave)-based --.

Column 6, Line 43, delete "is only, exemplary." and insert -- is only exemplary. --.

Column 9, Line 44, delete "17 overtime 18. The" and insert -- 17 over time 18. The --.

Column 11, Line 57, delete "of $A_r=s_4$" and insert -- of $\Delta r=s_4$ --.

Signed and Sealed this
Twenty-second Day of July, 2025

Coke Morgan Stewart
*Acting Director of the United States Patent and Trademark Office*